United States Patent [19]

Vadgama et al.

[11] Patent Number: 4,919,767
[45] Date of Patent: Apr. 24, 1990

[54] SENSOR AND METHOD FOR ANALYTE DETERMINATION

[75] Inventors: Pankaj M. Vadgama, Salford; Lian X. Tang, Newcastle-upon-Tyne, both of England

[73] Assignee: Imperial Chemical Industries PLC, London, United Kingdom

[21] Appl. No.: 228,153

[22] Filed: Aug. 4, 1988

[30] Foreign Application Priority Data

Aug. 4, 1987 [GB] United Kingdom ................ 8718430

[51] Int. Cl.⁵ .............................................. C12Q 1/00
[52] U.S. Cl. .................. 204/153.1; 204/403; 435/4; 435/288; 435/291; 435/817
[58] Field of Search ............... 435/817, 291, 4, 288; 204/1 E, 403

[56] References Cited

U.S. PATENT DOCUMENTS 3,979,274 9/1976 Newman ........................ 435/817 X
4,388,166 6/1983 Suzuki et al. ...................... 204/403
4,661,235 4/1987 Krull et al. ........................ 204/414
4,759,828 7/1988 Young et al. ...................... 204/1 T

OTHER PUBLICATIONS

"The Structure and Electrochemical Properties of a Polymer-Supported Lipid Biosensor", by Thompson et al., Analytica Chimica Acta, vol. 117, 1980, pp. 133-145.

Primary Examiner—G. L. Kaplan
Attorney, Agent, or Firm—Cushman, Darby & Cushman

[57] ABSTRACT

A sensor of the enzyme-electrode type comprising an electrode and a membrane permeable to liquids and solutes which is positioned between the electrode and a specimen containing the analyte to be determined, is characterized by the fact that a layer of a porous material, positioned in the membrane between the enzyme-containing layer and the specimen, has been treated to at least partially fill the pores with a liquid of limited volatility which is not significantly soluble in water and is to some degree a solvent for the analyte.

13 Claims, 7 Drawing Sheets

SENSOR AND METHOD FOR ANALYTE DETERMINATION

This invention relates to a sensor of the enzyme electrode type comprising an improved membrane and to an analytical method using the sensor.

Enzyme electrodes are increasingly used in medical and other laboratories particularly for the determination of materials such as glucose and urea in specimens of blood and other physiological fluids. Such electrodes are described in many publications notably an article by Clark and Lyons (Anals of the New York Acadamy of Science, 102, 29–45, 1962) and U.S. Pat. Nos. 3,539,455 and 3,979,274 to Clark and Newman respectively. Enzyme electrodes are generally used to determine materials which themselves are not electrochemically active but which in the presence of suitable enzymes take part in reactions which produce species which can be readily detected by the electrodes. In enzyme electrodes the enzymes are frequently located within polymeric materials in close proximity to the underlying electrode.

A considerable amount of research has been carried out in order to improve the properties of membranes for use in enzyme electrodes and many membranes for this purpose have been disclosed. An example of a type of membrane which is often used is the laminated membrane disclosed by Newman in U.S. Pat. No. 3,979,274. This membrane comprises a first or inner layer of an essentially homogeneous material, for example cellulose acetate, which can prevent the passage of materials of low molecular weight likely to interfere with the enzymic signal, a close adherent layer of the enzyme itself (with or without such other materials that may be blended with it), and a second layer (in this instance an outer layer) of a porous support film which can prevent the passage of cellular and colloidal elements.

The determination of glucose can be taken as an example of the determination of a material by an enzyme electrode. In the presence of the enzyme glucose oxidase the following reaction occurs:

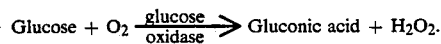

The hydrogen peroxide produced in this reaction passes through the first layer of a membrane such as that of U.S. Pat. No. 3,979,274 and can be determined using the electrode. Since the hydrogen peroxide produced is dependent upon the glucose present in a specimen, the glucose concentration can be determined using a suitably calibrated sensor.

To date a number of difficulties have limited the utility of enzyme electrodes and restricted the scale of their use in routine analysis of, e.g. blood samples. Significant among these difficulties is the limited linearity of the response of electrodes to analytes such as glucose or lactate which are substrates for the enzyme catalysed reactions. The response is linear only over a limited range of low concentrations of the analytes and hence the concentrations of the materials to be determined must be low and generally diluted samples must be used in specimens for analysis using enzyme electrodes. It is not always practicable to make diluted samples for routine analysis outside the laboratory and it would be impossible for invasive monitoring.

In our published European Patent Application No. 216577 we describe and claim a sensor for the determination of an analyte having a membrane between its electrode and a specimen of the analyte to be tested. Preferably the membrane is a membrane such as that of U.S. Pat. No. 3,979,274. However, in the membrane of the sensor of European application No. 216577 there is a restricted permeability layer of material between the enzyme-containing layer and the specimen which restricted permeability layer contains an area through which analyte can pass formed from a porous material of restricted permeability having a porosity which is not greater than 5%.

According to the present invention we provide a sensor of the enzyme-electrode type for the determination of an analyte, said analyte being convertible in the presence of an enzyme into a species which can be detected by the sensor, which comprises an electrode and a membrane permeable to liquids and solutes positioned between the electrode and a specimen containing the analyte, said membrane comprising a layer containing one or more enzymes and a layer of material positioned between the enzyme-containing layer and the specimen characterised in that said layer of material contains an area through which analyte can pass formed from a porous material which has been treated to fill its pores wholly or partially with a liquid thereby forming a supported liquid membrane.

Further according to the invention we provide a method for determining an analyte in a specimen which comprises contacting the specimen with the outer layer of a membrane, permeable to liquids and solutes and comprising one or more enzymes, in the presence of which the analyte is convertible into a species detectable by a sensor which incorporates the membrane, and one or more layers of material, and measuring the response of the sensor to the species, characterised in that a layer in the membrane between the enzyme and the specimen contains an area through which analyte can pass formed from a porous material which has been treated to fill its pores wholly or partially with a liquid thereby forming a supported liquid membrane.

The liquid is of limited volatility and is not significantly soluble in water so that loss of the liquid from the membrane via evaporation and/or dissolution is reduced and hence the stability of the liquid membrane enhanced. The liquid is to some degree a solvent for the analyte so that the analyte may pass through the liquid in the liquid membrane to reach the enzyme.

The phrase "liquid of limited volatility" includes systems in which a volatile liquid is held below another liquid having limited volatility, although such systems have limited utility in the sensors of the invention. Preferably the liquid of limited volatility is either not a solvent for interfering species such as ascorbic acid which will give rise to signals interfering with those from the analyte or is a solvent for such interfering species only to a limited extent.

The liquid may be in the form of a solution. The liquid may comprise a lipid or a fatty acid ester. The liquid treated layer can be formed by dipping a membrane in a suitable liquid, particularly lipid solutions, e.g. in n-butanol or n-decane or mixtures as solvents. Preferred lipids for liquid treatments are isopropyl myristate (IPM) and lecithin. These lipids when used in concentrations of approximately 0.5 mM will allow catechol and glucose to pass through them but are substantially impermeable to interfering species such as ascorbic acid, uric acid, hydrogen peroxide and paracetamol.

A suitable technique for forming the treated layer is to dip the membrane into the liquid, e.g. a lipid solution for a short time, e.g. 2 to 4 minutes. After this time the membrane is removed using a tissue before the membrane is fitted to the electrode. It has been found that the liquid treated membrane is quite stable with time.

The sensor of the invention is selective with regard to analytes and gives a response which is linear over a range similar to that of our published European Patent Application No. 216577. It enables this similar degree of linearity to be achieved using membranes with layers of restricted permeability which have larger pores and/or greater porosities than those of the membranes of European Application No. 216577.

The treated area causes the layer containing it to have restricted permeability. Preferably all or a major proportion of the effective area of this layer has been treated.

In its most simple form the membrane in the sensor of the invention consists of the enzyme-containing layer and the treated layer. The treated layer is the outer layer in this simple form of membrane and is contacted directly by the specimen in the method of the invention for determining an analyte.

However, it is possible for the membrane to be a laminated membrane of the type of which that disclosed in U.S. Pat. No. 3,979,274 is an example. Such a membrane comprises a first or inner layer of material positioned between the enzyme-containing layer and the electrode, the enzyme-containing layer and a second layer of material on the other side of the enzyme-containing layer which second layer is the treated layer.

Hereafter in this specification the sensor of the invention which is described will contain a laminated membrane of the type of which the membrane described in U.S. Pat. No. 3,979,274 is an example having first and second layers the treated layer being the second layer.

It should be understood that the membranes in the sensor of the invention can contain more than two layers of material in addition to the enzyme-containing layer. For instance the second layer, i.e. the treated layer is not necessarily the outermost layer of the membrane. There may be a further layer or layers of material, i.e. third, fourth etc layers, between the second layer or treated layer and the specimen. Often however the second layer will be the outer layer and its outer face will be contacted by the specimen.

Generally the porous material of the treated layer will be a polymeric material but other suitable materials may be used. Thus the treated layer may be formed from porous glass, a metal, e.g. a sintered metal, having pores cut by lasers or porous etched and sintered ceramics such as aluminas.

Suitably the treated layer of material is formed from material having a porosity in the range 0.05 to 20%.

The pore size is selected so that the liquid of limited volatility fills the pore wholly or partially to form a supported liquid membrane. The mean diameters of the pores may be less than 5 $\mu$m, and are preferably equal to or less than 3 $\mu$m. For example the mean diameters of the pores may be in the range 3 $\mu$m to 0.05 $\mu$m, particularly for the case where the liquid comprises isopropyl myristate and the layer is formed from a polycarbonate.

The sensor of the invention may have a detachable membrane or it may be a disposable sensor with an adherent membrane. Materials used in the formation of suitable electrodes for the sensors include inert metals and/or carbon.

When the sensor incorporates a laminated membrane of the type disclosed in U.S. Pat. No. 3,979,274 the first layer which is to be located between the enzyme layer and the electrode is suitably formed from polymethylmethacrylate, polyurethane, cellulose acetate or another porous material which will restrict or prevent passage of electroactive interfering compounds such as ascorbic acid and tyrosine. Suitably the first layer has a thickness in the range 0.1 microns to 1.0 microns. Preferably the membrane contains a layer formed from a polyarylsulphone or a polyarylketone as described in our published European Application No. 225094.

Suitable porous materials for the second layer include porous polycarbonates, polyurethanes, and modified cellulose particularly cellulose nitrate, cellulose acetate and regenerated cellulose.

The enzyme present in the sensor of the invention may be located in the membrane in any suitable manner. Preferably in a laminated membrane it is present between the first and second layers of material and forms the bond between them. In this situation, and also generally, the enzyme is preferably immobilised in a gel. A very suitable material for this purpose is glutaraldehyde; proteins such as albumin and other materials may also be included. In order to facilitate the obtaining of rapid stable readings from the sensor it is preferred that the enzyme-containing layer is thin, i.e. not greater than 5 microns thick.

The enzyme to be used in the sensor of the invention will depend upon the analyte whose concentration is to be determined. If the analyte is glucose then the enzyme will be for example glucose oxidase. Other enzymes which may be present include uricase and lactate oxidase for determination of uric acid and lactic acid respectively. Enzyme systems comprising two or more enzymes may also be present.

A laminated membrane for use in the sensor of the invention for the determination of glucose may be prepared by a method including the following steps:

1. A porous polycarbonate film having a porosity of less than 20% and pores of diameter less than 10 $\mu$m and preferably less than 5 $\mu$m is dipped in isopropyl myristate in n-butanol for 3 minutes to treat it. When removed from the solution, excess liquid is removed from the film using a tissue;
2. 1 mg glucose oxidase is dissolved in 50 $\mu$l of (100 mg/ml) albumin;
3. 3 $\mu$l of 12.5% glutaraldehyde solution is mixed with 3 $\mu$l of enzyme/albumin mixture on a glass microscope slide;
4. 1 $\mu$l of the mixture produced in the previous step is applied to one face of the 1 cm$^2$ polycarbonate produced in step 1;
5. The other surface of the enzyme layer is covered immediately with a thin cellulose acetate film and the resulting laminated membrane is clamped for 3 minutes between glass slides;
6. The membrane is applied to a platinum electrode to form the sensor of the invention, the cellulose acetate film being nearest to the electrode and forming the first layer.

Use of the method of the invention gives the advantage of an increase in the concentration range over which a graph of concentration against sensor response is linear. With conventional methods linearity was generally extended only up to approximately a concentration of 3 m mol per liter for glucose. Using the method of the invention linearity is increased and the range extends to glucose concentrations of 50 m mol per liter and even higher. This is achieved through restriction of substrate entry into the enzyme layer and therefore with some loss of sensitivity. Thus the range covers the concentrations of glucose which can be anticipated in blood samples thereby enabling blood glucose levels to be determined more readily. This is a considerable advantage in situations where large numbers of determinations must be made regularly and with minimal sample preparation. Linearity is also extended by applying to the second layer of the membrane a medium comprising an organo-silane having reactive groups as described in our published European Patent Application No. 204468. This treatment may be applied to the second layer of the membrane in the sensor of the present invention to produce a combined effect and further improved linearity.

These and other objects of the present invention will be described in detail herewith with respect to the accompanying drawings, in which.

Figure 1:
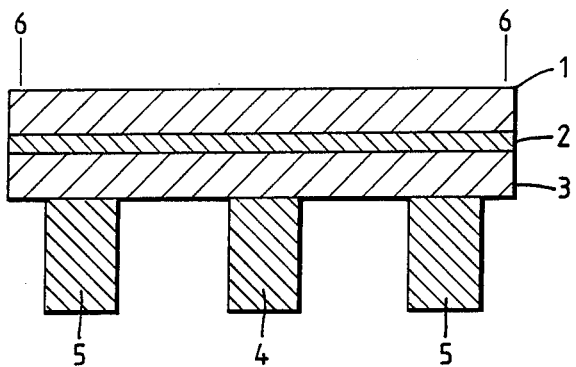
FIG. 1 shows a diagram of the sensor used according the present invention.

The invention is illustrated by FIG. 1 of the accompanying drawings.

In FIG. 1, reference numeral 1 is the second layer of the membrane formed from a polycarbonate film treated with a 30% solution of isopropyl myristate (IPM), 2 is a layer of glucose oxidase enzyme dissolved in albumin and mixed with glutaraldehyde, 3 is the first layer formed from cellulose acetate, 4 is the platinum working electrode and 5 is the silver reference electrode. 1, 2 and 3 together form a laminated membrane. Platinum working electrode 4 acts as an anode whilst silver reference electrode 5 acts as a cathode. The membrane is held in place on the electrode by a perspex ring pressing down on outer layer 1 towards its outer edges at 6.

The use of the sensor shown in FIG. 1 is illustrated in the following example:

EXAMPLE

Experiments were carried out using sensors having membranes prepared as described above. The second or outer layers of the membranes used were formed from polycarbonate film treated by dipping in lipid solutions in n-butanol, n-decane and mixture of these solvents. Lipids used were lecithin and isopropyl myristate. These treated membranes were found to be readily permeable to catechol but only permeable with difficulty to species such as hydrogen peroxide, ascorbic acid, paracetamol and phiroglucinol (concentrations of the species used were 0.5 mM). This is illustrated in the following table which shows the reduction in signal size observed for each of the interferring species when polycarbonate membranes with pore sizes 0.8 μm and 0.2 μm are treated with IPM.

| SPECIES | Reduction in Signal size (%) | |
|---|---|---|
| | 0.8 μm pore size | 0.2 μm pore size |
| Hydrogen Peroxide | 86.3 | 98.5 |
| Ascorbic acid | 94.65 | 100 |
| Uric Acid | 91.31 | |
| Paracetamol | 56 | 82 |
| Phiroglucinol | 66.6 | 95 |

The treated membranes were permeable to glucose although the magnitude of the response registered by the sensor was reduced. It was found that the range of linearity of the response obtained in a series of experiments with different glucose concentrations was increased in treated membranes.

This is illustrated by the graphs shown in FIGS. 2 to 10 of the drawings in which response magnitude is plotted against glucose concentration (mM). The treated membranes referred to are polycarbonate membranes treated with IPM.

Figure 2:
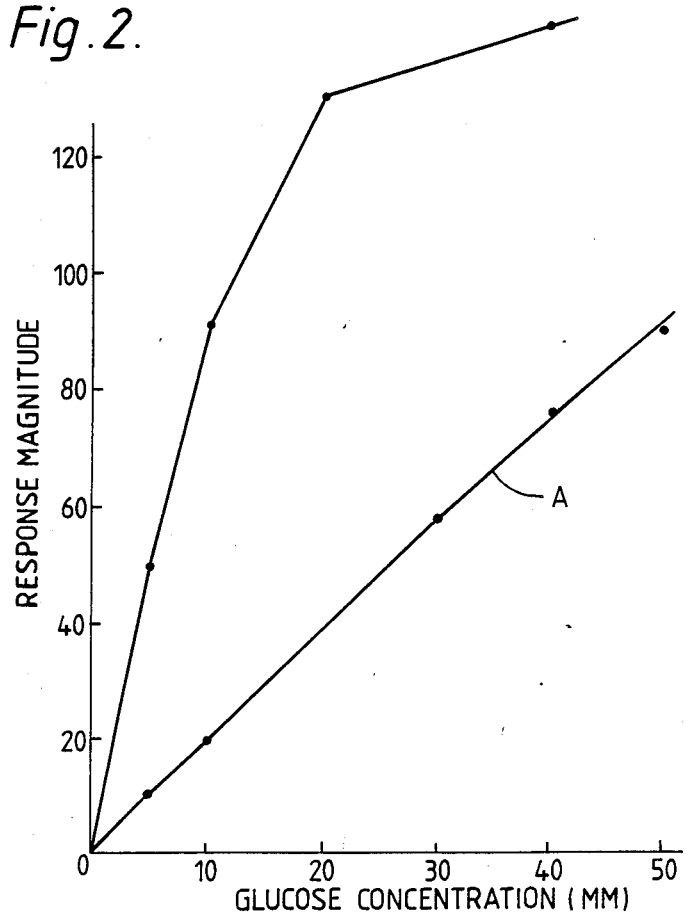
FIG. 2 shows the response obtained with a treated membranes in contrast with the untreated membrane.

As shown in FIG. 2, the response (in arbitrary units) obtained with membranes treated with IPM (plot A) is linear up to at least 50 mM, in contrast to the response (plot B) obtained with the untreated membrane.

Figure 3:
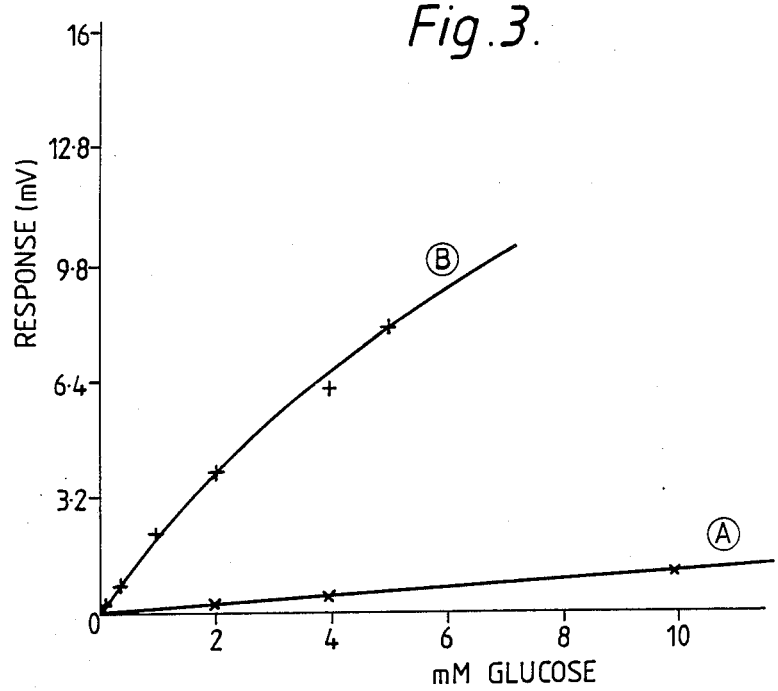
FIG. 3 shows a response obtained with an untreated membrane of 2 μm as compared with a treated membrane.

FIGS. 3 to 10 further illustrate the result shown in FIG. 2 and also show the effect of pore size on linearity of response. In FIG. 3, Plot B is the response obtained with an untreated membrane having a pore size of 2 μm, and Plot A is the response obtained with a membrane treated with IPM. Linearity is thus increased for the treated membrane.

Figure 4:
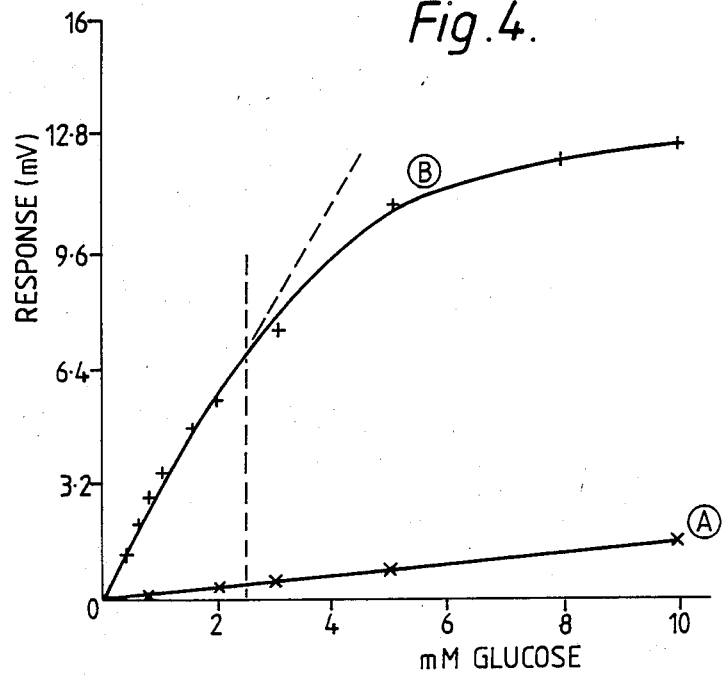
FIG. 4 shows a response for untreated versus treated membrane 2 μm.

FIG. 4 shows the response obtained with membrane having a pore size of 0.2 μm. The untreated membrane gives a linear response only up to a concentration of just over 2 mM glucose (see Plot B); whereas the treated membrane (Plot A) gives a linear response at least up to a concentration of 10 mM.

Figure 5:
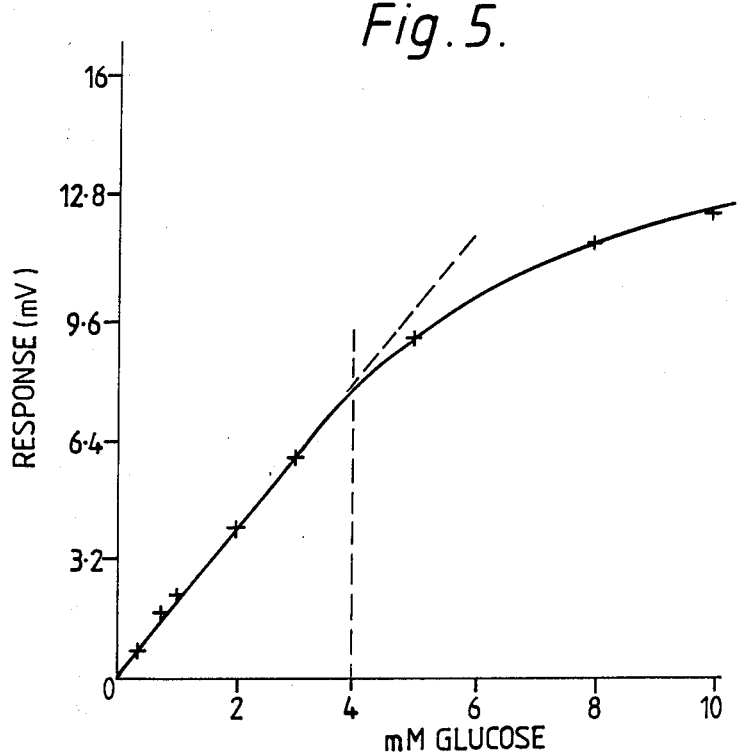
FIG. 5 shows the linearity of response as compared with concentration of glucose for an untreated membrane of 0.05 μm.
Figure 6:
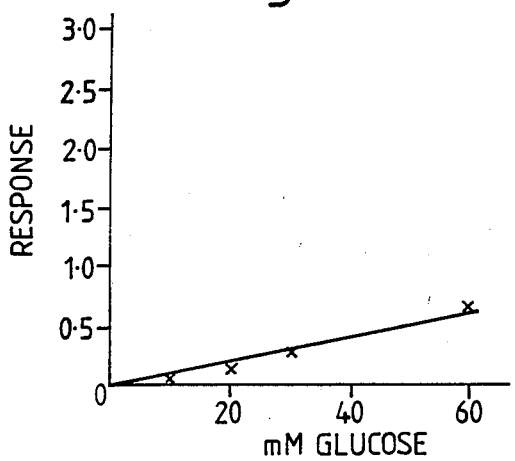
FIG. 6 shows the same linearlity for a treated membrane.

As shown in FIGS. 5 and 6 the response obtained with an untreated membrane having a pore size of 0.05 μm is linear up to about a concentration of 4 mM glucose (FIG. 5); whereas the treated membrane gives a linear response up to at least 60 mM glucose (FIG. 6).

Figure 7:
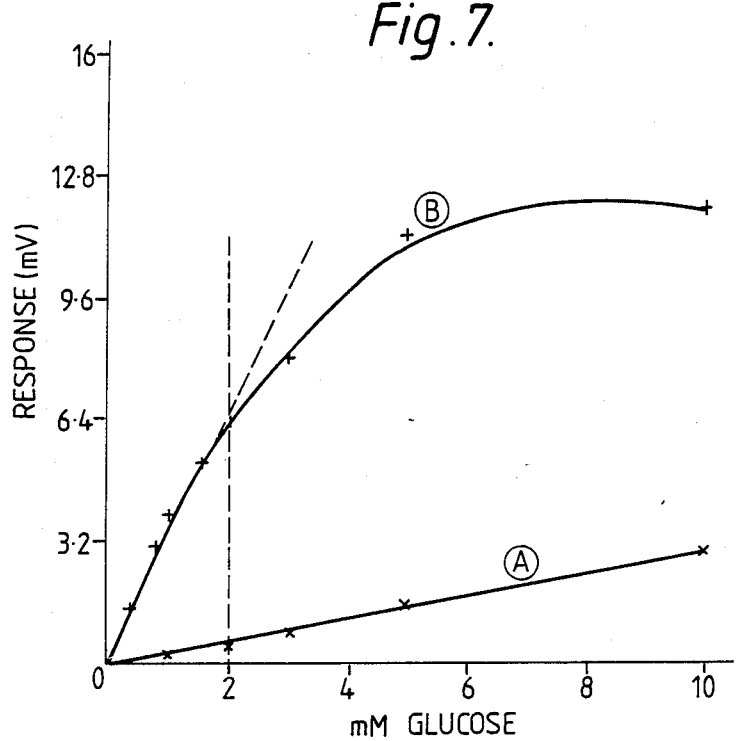
FIG. 7 shows a response with pore size of 0.8 μm for an untreated membrane, and shows the linearity of response.
Figure 8:
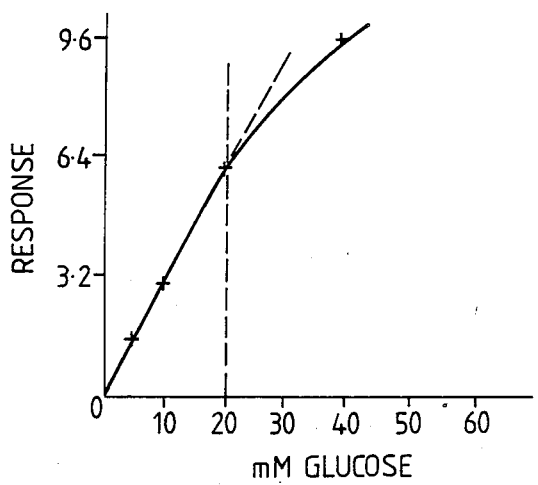
FIG. 8 shows the same linearlity for a treated membrane.

The response obtained with membranes having a pore size of 0.8 μm is shown in FIGS. 7 and 8. As shown in FIG. 7, the untreated membrane gives a linear response only up to a concentration of 2 mM glucose (Plot B). However, a membrane treated with 1PM gives a linear response up to a concentration of about 20 mM glucose (see Plot A FIG. 7, and FIG. 8).

Figure 9:
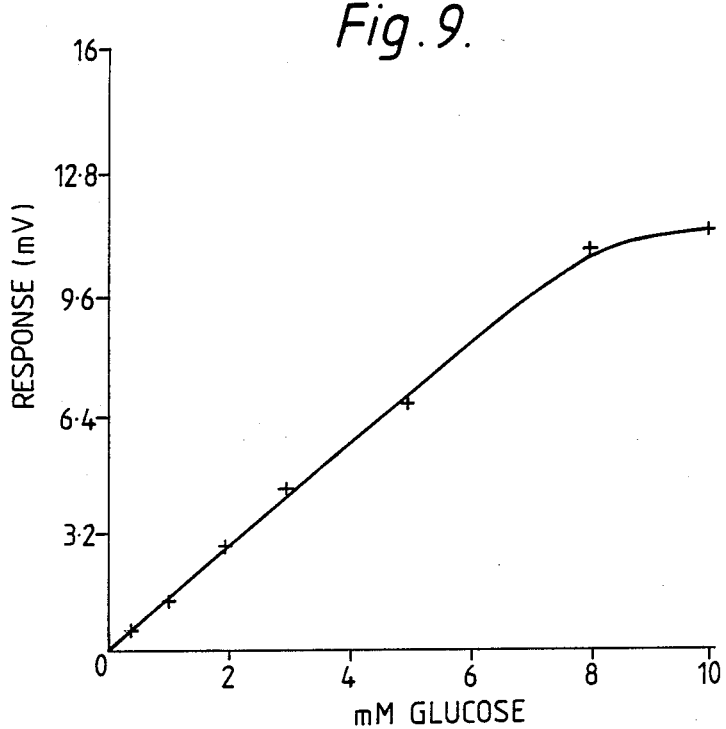
FIGS. 9 and 10 show response for a pore size of 0.015 μm for untreated and treated membranes, respectively.
Figure 10:
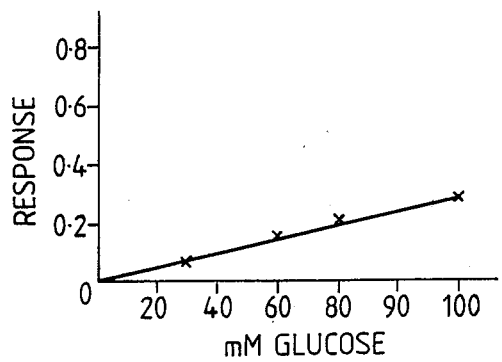

Similarly, an increase in linearity of response was observed with a pore size of 0.015 μm when treated with 1PM—see FIG. 9 (untreated membrane) and FIG. 10 (treated membrane).

The experiments referred to above illustrate that the range of linearity is increased with treated membranes. It was also observed that the upper concentration limit of the range may vary with concentration of the liquid. For example an untreated polycarbonate membrane (pore size 0.2 μm) gave a linear response up to just over 2 mM glucose; whereas a membrane treated with 100% IPM was linear up to 30 mM glucose and a membrane treated with 90% 1PM/10% n-decanol was linear up to at least 60 mM glucose.

Experiments also showed that membranes treated with the fatty acid esters methyl oleate and methyl linoleate increased lineaty of response in a similar way to IPM. Membranes treated with lecithin also behaved in a similar fashion to these treated with IPM.

We claim:

1. A sensor of the enzyme-electrode type for the determination of an analyte in a sample, which analyte is convertible in the presence of an enzyme into a species which is detectable by the sensor, which sensor comprises an electrode and a membrane permeable to liquids and solutes which is positioned between the electrode and a specimen containing the analyte, which membrane comprises a first layer containing at least one enzyme and a second layer positioned between the enzyme-containing layer and the specimen, wherein said second layer contains an area through which analyte can pass, in the form of a liquid membrane formed from a porous material of which the pores have been at least partially filled with a liquid having the ability to pass the analyte while rejecting other species in the sample.

2. A sensor according to claim 1, wherein said membrane further comprises a third layer of material disposed between the enzyme-containing layer and the electrode.

3. A sensor according to claim 2, wherein said third layer is formed from a material selected from the group consisting of polymethylmethacrylate, polyurethane and cellulose acetate.

4. A sensor according to claim 1, wherein the porous material is selected from the group consisting of polycarbonates, polyurethanes and modified celluloses.

5. A sensor according to claim 1, wherein the porous material has a porosity within the range from 0.05 to 20 percent.

6. A sensor of the enzyme-electrode type for the determination of an analyte in a specimen containing said analyte, said analyte being convertible in the presence of an enzyme into a species detectable by the sensor, which sensor comprises an electrode and a membrane permeable to liquids and solutes which is positioned between the electrode and the specimen, said membrane comprising an enzyme-containing layer, a layer of material disposed between said enzyme-containing layer and said electrode and a layer disposed between said enzyme-containing layer and said specimen and having an area of a porous material of average pore diameter less than 5 μm, said pores being at least partially filled with a non-aqueous liquid having the ability to pass the analyte while rejecting other species in the specimen.

7. A sensor according to claim 6, wherein the liquid comprises a lipid.

8. A sensor according to claim 7, wherein said lipid is selected from the group consisting of isopropyl myristate and lecithin.

9. A sensor according to claim 6, wherein the liquid comprises an ester of a fatty acid.

10. A sensor according to claim 9, wherein the fatty acid ester is selected from the group consisting of methyl oleate and methyl linoleate.

11. A sensor according to claim 6, wherein the membrane contains a layer formed from a polymeric material selected from the group consisting of polyarylsulphones and polyarylketones.

12. An enzyme-electrode sensor for determining an analyte in a specimen, which analyte is convertible in the presence of an enzyme into a species detectable by the sensor, which sensor comprises an electrode, a first layer of a material selected from polymethylmethacrylate, polyurethane and cellulose acetate, disposed between the electrode and the specimen, an enzyme-containing second layer overlying said first layer, and a porous third layer overlying said second layer, which porous layer comprises a material selected from polycarbonates, polyurethanes and modified celluloses, has an average pore diameter less than 5 μm and has said pores at least partially filled with a liquid comprising a lipid or a fatty acid ester.

13. A method for determining an analyte in a specimen which comprises contacting the specimen with the outer layer of a membrane, permeable to liquids and solutes and comprising one or more enzymes, in the presence of which the analyte is convertible into a species detectable by a sensor which incorporates the membrane, and one or more layers of material, and measuring the response of the sensor to the species, characterized in that a layer in the membrane between the enzyme and the specimen contains an area through which analyte can pass formed from a porous material which has been treated to fill its pores wholly or partially with a liquid which has the ability to pass the analyte while rejecting other species in the specimen.

* * * * *